US008369005B2

(12) United States Patent
Yamamoto

(10) Patent No.: US 8,369,005 B2
(45) Date of Patent: Feb. 5, 2013

(54) FIBER LIGHT SOURCE

(75) Inventor: Eiji Yamamoto, Tokyo (JP)

(73) Assignee: Olympus Corporation, Tokyo (JP)

( * ) Notice: Subject to any disclaimer, the term of this patent is extended or adjusted under 35 U.S.C. 154(b) by 310 days.

(21) Appl. No.: 12/176,040

(22) Filed: Jul. 18, 2008

(65) Prior Publication Data

US 2009/0039756 A1 Feb. 12, 2009

(30) Foreign Application Priority Data

Aug. 10, 2007 (JP) ................................ 2007-210188

(51) Int. Cl.
*H04B 10/17* (2006.01)
*G02B 6/32* (2006.01)
*G02B 6/38* (2006.01)

(52) U.S. Cl. ............ 359/341.1; 385/55; 385/66; 385/74

(58) Field of Classification Search ............... 359/341.1; 385/55, 58, 61, 66, 70, 73, 141, 142; 372/6
See application file for complete search history.

(56) References Cited

U.S. PATENT DOCUMENTS 7,020,378 B2 3/2006 Poisel et al.
2005/0163424 A1 7/2005 Chen
2006/0263019 A1 11/2006 Negishi et al.
2007/0297190 A1 12/2007 Ng

FOREIGN PATENT DOCUMENTS

JP 6-51126 A 2/1994
JP 2000-275444 A 10/2000
JP 2003-19112 1/2003
JP 2005-328921 12/2005
JP 2008141066 A * 6/2008
WO WO 00/32982 6/2000

OTHER PUBLICATIONS

Japanese Office Action dated Aug. 21, 2012 in counterpart Japanese Patent Application No. 2007-210188.

* cited by examiner

*Primary Examiner* — Eric Bolda
(74) *Attorney, Agent, or Firm* — Scully, Scott, Murphy & Presser, P.C.

(57) ABSTRACT

A fiber light source includes an exciting light source to emit exciting light and an optical fiber to guide the exciting light. The optical fiber contains, in a portion in the longitudinal direction, phosphors that emit fluorescence in accordance with the application of exciting light. The optical fiber includes a high reflection film covering the outer surface of a portion through which fluorescence emitted from the phosphor travels.

10 Claims, 12 Drawing Sheets

FIBER LIGHT SOURCE

CROSS-REFERENCE TO RELATED APPLICATIONS

This application is based upon and claims the benefit of priority from prior Japanese Patent Application No. 2007-210188, filed Aug. 10, 2007, the entire contents of which are incorporated herein by reference.

BACKGROUND OF THE INVENTION

1. Field of the Invention

The present invention relates to a fiber light source.

2. Description of the Related Art

There is known a fiber light source comprising an optical fiber containing phosphors that emit fluorescence in accordance with the application of exciting light and a light source to emit exciting light traveling through the optical fiber. In the fiber light source, the phosphors emit fluorescence while the exciting light travels through the optical fiber. The emitted fluorescence travels through the optical fiber and exits as a light beam from the exit end. The application of this fiber light source to the illumination of an endoscope has been proposed.

BRIEF SUMMARY OF THE INVENTION

A fiber light source according to the present invention comprises an exciting light source to emit exciting light and an optical fiber to guide the exciting light. The optical fiber contains, in a portion in the longitudinal direction, phosphors that emit fluorescence in accordance with the application of exciting light. The optical fiber includes a high-reflection film covering the outer surface of a portion through which fluorescence emitted from the phosphor travels.

Advantages of the invention will be set forth in the description that follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

The embodiments of the present invention will be described below with reference to the views of the accompanying drawing.

First Embodiment

Figure 1:
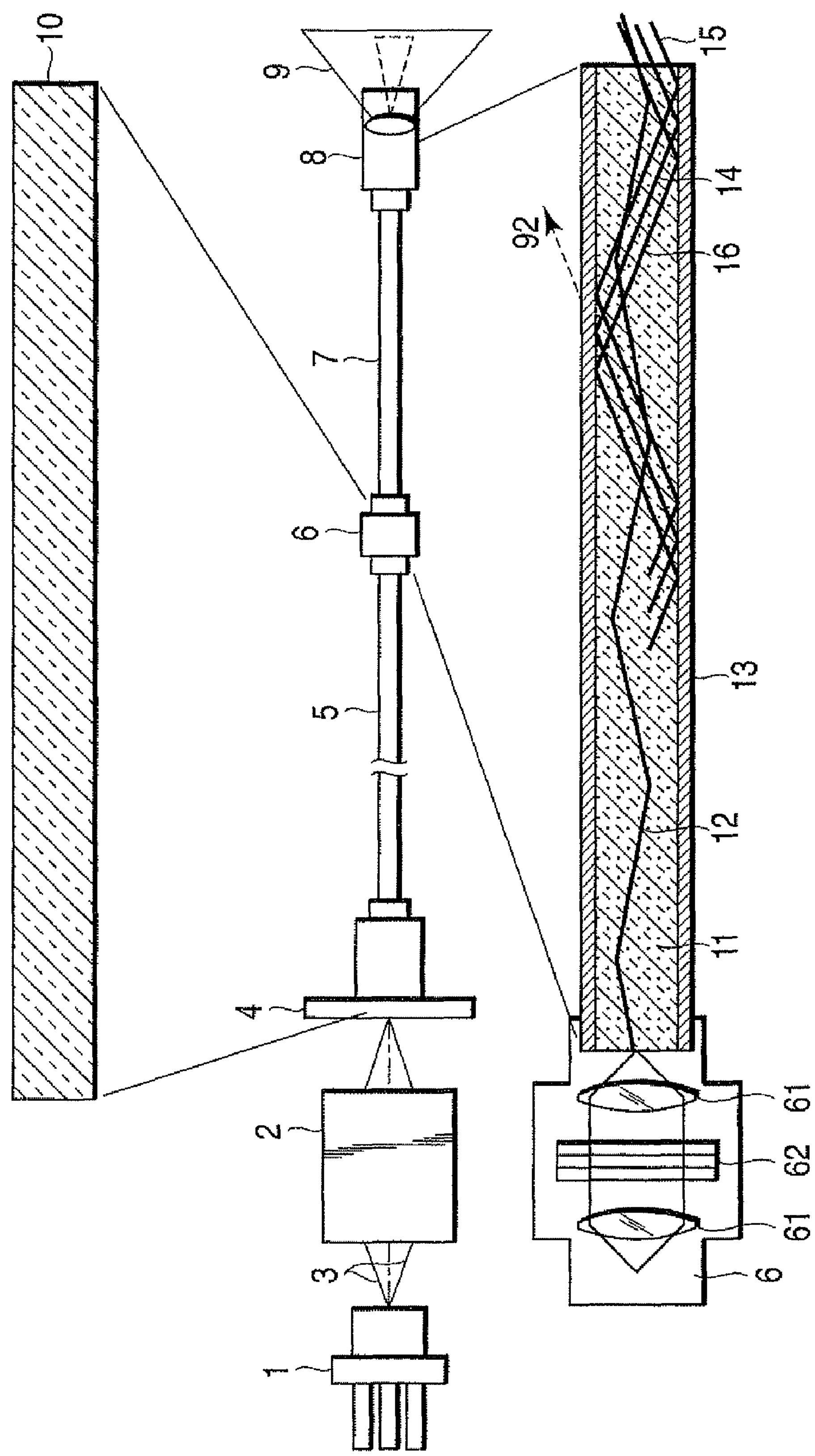
FIG. 1 shows a fiber light source according to the first embodiment.

FIG. 1 shows a fiber light source according to the first embodiment. The fiber light source includes a semiconductor laser 1, a GRIN lens 2, a first optical fiber 5, and a second optical fiber 7. The semiconductor laser 1 functions as an exciting light source to emit exciting light. The GRIN lens 2 focuses laser light emitted from the semiconductor laser 1 and applies the light to the input end of the first optical fiber 5. A fiber connector 4 is mounted on the input end portion of the first optical fiber 5. The first optical fiber 5 and the second optical fiber 7 are mechanically connected by a connector 6, so as to be optically coupled. The first optical fiber 5 has a light guide member 10. The second optical fiber 7 has a light guide member 11 and a metal film 13 covering the outer surface of the light guide member 11. The light guide member 11 contains phosphors that emit fluorescence in accordance with the application of exciting light. In contrast, the light guide member 10 contains no phosphor. The light guide members 10 and 11 may comprise, for example, members with core/clad structures that conduct light. However, the present invention is not limited to this, and may use any structures as long as they conduct light. The metal film 13 functions as a high-reflection film. A connector 8 is mounted on the output end portion of the second optical fiber 7.

The first optical fiber 5 and the second optical fiber 7 are detachably attached through the connector 6. In the connector 6, a dichroic mirror 62 that transmits exciting light and reflects fluorescence is placed between a pair of lenses 61. The dichroic mirror 62 is an optical functional component to transmit exciting light and to reflect fluorescence. The dichroic mirror 62 is placed between the semiconductor laser 1 as an exciting light source and the second optical fiber 7 containing phosphors. The phosphors contained in the second optical fiber 7 include, for example, different types of phosphors that are excited by the exciting light to emit fluorescence components with different optical spectra. These different types of phosphors may be contained in the same region of the second optical fiber 7 in the longitudinal direction or may be respectively contained in different regions of the second optical fiber 7 in the longitudinal direction.

The semiconductor laser 1 emits laser light in the beam shape shown by a divergent region 3. The emitted laser light is focused by the GRIN lens 2 and strikes the input end of the first optical fiber 5. The incident laser light travels through the first optical fiber 5 and then reaches the second optical fiber 7. The light then travels through the second optical fiber 7. When laser light 12 travels through the second optical fiber 7, the phosphors in the light guide member 11 of the second optical fiber 7 emit fluorescence in accordance with the application of the laser light 12, i.e., exciting light. The fluorescence includes red light 14, green light 15, and blue light 16. That is, the phosphors emit fluorescence of multiple colors. The fluorescence travels through the second optical fiber 7 and reaches the exit end of the second optical fiber 7. The fluorescence that has reached the exit end exits as an applied beam 9 through the connector 8.

Figure 11A:
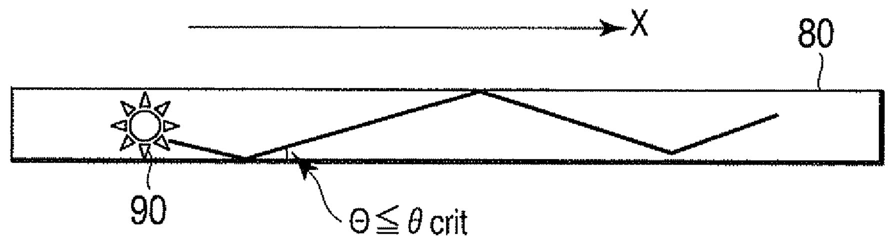
FIG. 11A shows fluorescence that travels in an optical fiber upon repetitive total reflection.
Figure 11B:
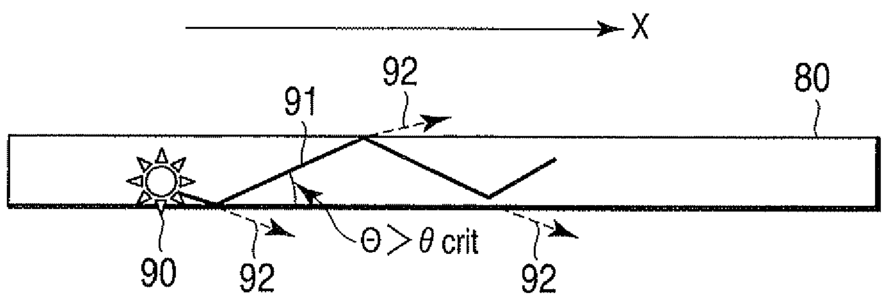
FIG. 11B shows fluorescence containing components reflected by the surface of the optical fiber and a component that is transmitted through the surface of the optical fiber and scattered.
Figure 11C:
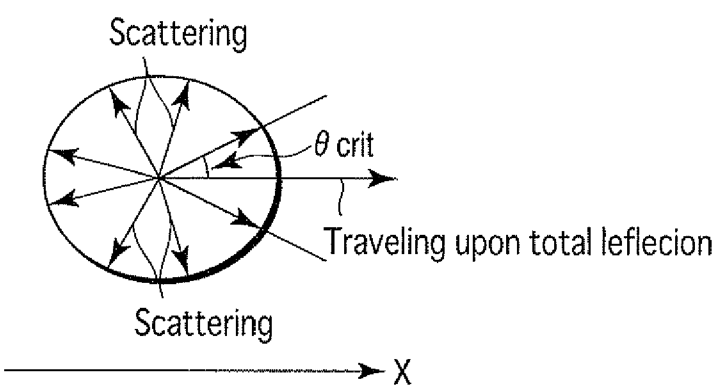
FIG. 11C is a schematic view showing a component traveling upon total reflection and scattered components.

A loss in a general optical fiber having no high-reflection film on the outer surface will be described below. As shown in FIG. 11A, assume that fluorescence generated at a point 90 in a fluorescence fiber 80 is applied at angle $\theta$ with respect to the longitudinal direction of the fluorescence fiber 80 toward the exit end. The angle $\theta$ will be referred to as a radiation angle hereinafter. The component represented by $|\theta| \leqq \theta crit$ (where $\theta crit$ is the critical angle of total reflection at the surface of the optical fiber) travels in the optical fiber upon repetitive total reflection. Assume that no light absorption or surface scattering occurs in an optical fiber. In this case, the optical fiber guides light without any loss. In contrast, as shown in FIG. 11B, the component represented by $|\theta| > \theta crit$ contains a component 91 reflected by the surface of the optical fiber and a component 92 that is transmitted through the surface of the optical fiber and scattered. For this reason, the fluorescence is attenuated at every surface reflection. FIG. 11C schematically shows this phenomenon with a component that travels upon total reflection at the radiation angle and invalid components, i.e., components that travel while being scattered and components that return to the light source side. Assume that $\theta crit = 45°$, which is a general value. In this case, according to approximation from a solid angle, a component traveling upon repetitive surface reflection, which is shown in FIG. 11C, corresponds to the ratio of the solid angle of the portion indicated by $\theta crit$ to the total solid angle, and hence the light is attenuated to approximately 1/7, which is obviously very small.

In this embodiment, the outer surface of the light guide member 11 is covered with the metal film 13 that is a high-reflection film. For this reason, if the radiation angle is given by $\theta < 90$ when a phosphor in the second optical fiber 7 emits fluorescence, the light is strongly reflected by the outer surface of the light guide member 11 even if $|\theta| > \theta crit$. The component 92 transmitted through the outer surface of the second optical fiber 7 is suppressed. That is, the second optical fiber 7 efficiently guides fluorescence while suppressing the scattering of the fluorescence.

The metal film 13 is good in heat dissipation characteristic for the heat generated by phosphors and the like. In addition, the metal film 13 easily provides a stably high reflectance unless it is very thin. Furthermore, since the reflectance of the metal film 13 does not strongly depend on the wavelength of light, a stable reflectance can be easily achieved.

Of the fluorescence emitted from the phosphors in the light guide member 11, a fluorescence component returning to the exciting light source side is reflected by the dichroic mirror 62 in the connector 6 and travels toward the exit end of the second optical fiber 7. This allows more efficient light guiding.

The structure of the second optical fiber 7 facilitates reducing the diameter, and comprises a single fiber. Note, however, that this fiber is thick enough to be resistant to breakage as compared with an optical fiber comprising a fiber bundle.

Since the light guide member 11 of the second optical fiber 7 contains phosphors distributed in the longitudinal direction, the heat generated in the process of absorption of exciting light by the phosphors is dissipated. This facilitates heat dissipation design and suppresses deterioration in the fiber due to heat generation. In addition, for a medical endoscope, the temperature of the outer surface of the endoscope must be equal to approximately 40° C. or less. A medical endoscope using the fiber light source of this embodiment as a light source achieves a high heat dissipation effect and facilitates heat dissipation design. This reduces a rise in the temperature of the outer surface of the endoscope even at the time of a high optical output. That is, the fiber light source of this embodiment is suitably used as the light source of a medical endoscope.

Since the fiber light source of this embodiment emits exciting light and fluorescence of multiple colors, light with a wide color band can be used.

This embodiment can be variously modified. Although the exciting light source comprises a semiconductor laser, it can comprise another type of laser light source. Without any consideration of coupling efficiency, the exciting light source may comprise a light source such as an LED. Although the optical element that couples applied light from the exciting light source to the optical fiber comprises a GRIN lens, it can be replaced by another type of element that has a focusing effect. An optical component that shapes a light beam can be placed at the exit end portion of the second optical fiber 7 to shape an applied light beam.

As another modification of the second optical fiber 7, optical fibers that differ in the contents and types of phosphors may be prepared. Detachably attaching the second optical fibers 7 to the connector 6 can implement a fiber light source having various optical spectra. Changing the content of phosphor can change the intensity ratio between exciting light and fluorescence. In addition, changing the type of phosphor allows to select a fluorescence wavelength or a fluorescence spectrum.

Figure 1A:
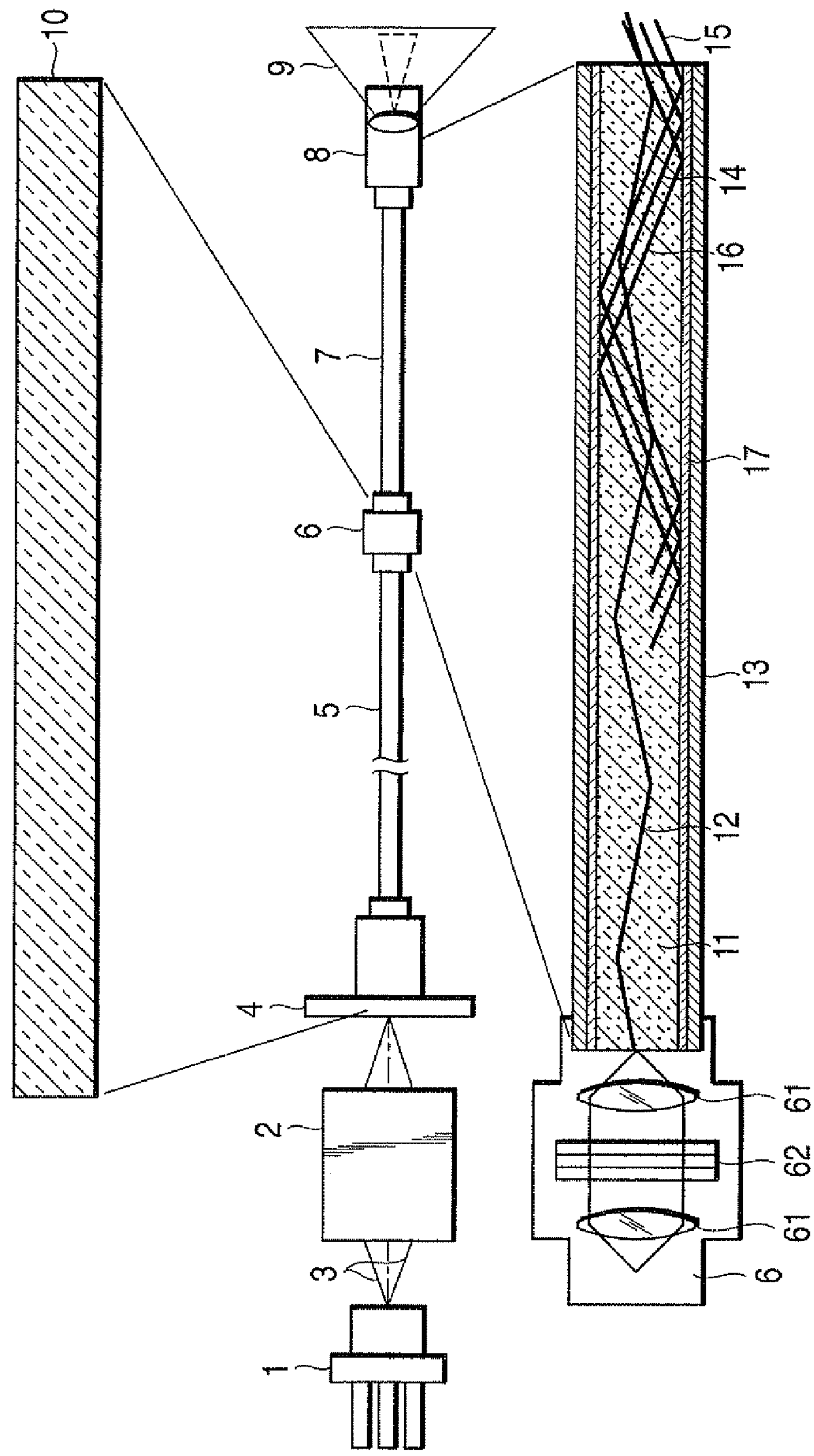
FIG. 1A shows a fiber light source according to a modification of the first embodiment.

In addition, a filter may be placed at the exit end portion of the second optical fiber 7 or in a path from the semiconductor laser 1 to the exit end portion of the second optical fiber 7 to shut off exciting light or limit the wavelength of fluorescence. Further, as shown in FIG. 1A, a dielectric film 17 may be placed between the light guide member 11 and the metal film 13 to prevent light scattering/absorption by the metal film.

Although phosphors are contained in the entire portion of the light guide member 11 in the longitudinal direction, phosphors may be contained in only part of the light guide member 11 in the longitudinal direction. The density of phosphors may be uniform in the longitudinal direction of the light guide member 11 or may be changed in the longitudinal direction of the light guide member 11.

Although the light guide member 11 comprises the single light guide member containing various types of phosphors, the light guide member 11 may comprise light guide members that respectively contain different types of phosphors and are arranged side by side in the longitudinal direction.

The phosphors may be phosphors that emit fluorescence with a predetermined wavelength or phosphors that emit fluorescence of a color complementary to that of exciting light. When a phosphor emits fluorescence of a color complementary to that of exciting light, since the fiber light source emits exciting light and fluorescence of a color complementary to that of the exciting light, the source can be used as a pseudo white illumination. When a phosphor emits fluorescence having a predetermined wavelength, since the fiber light source emits light having a specific wavelength, the light can be used as an analytical light source.

The embodiments described in this specification can be combined unless otherwise specified.

Second Embodiment

Figure 2:
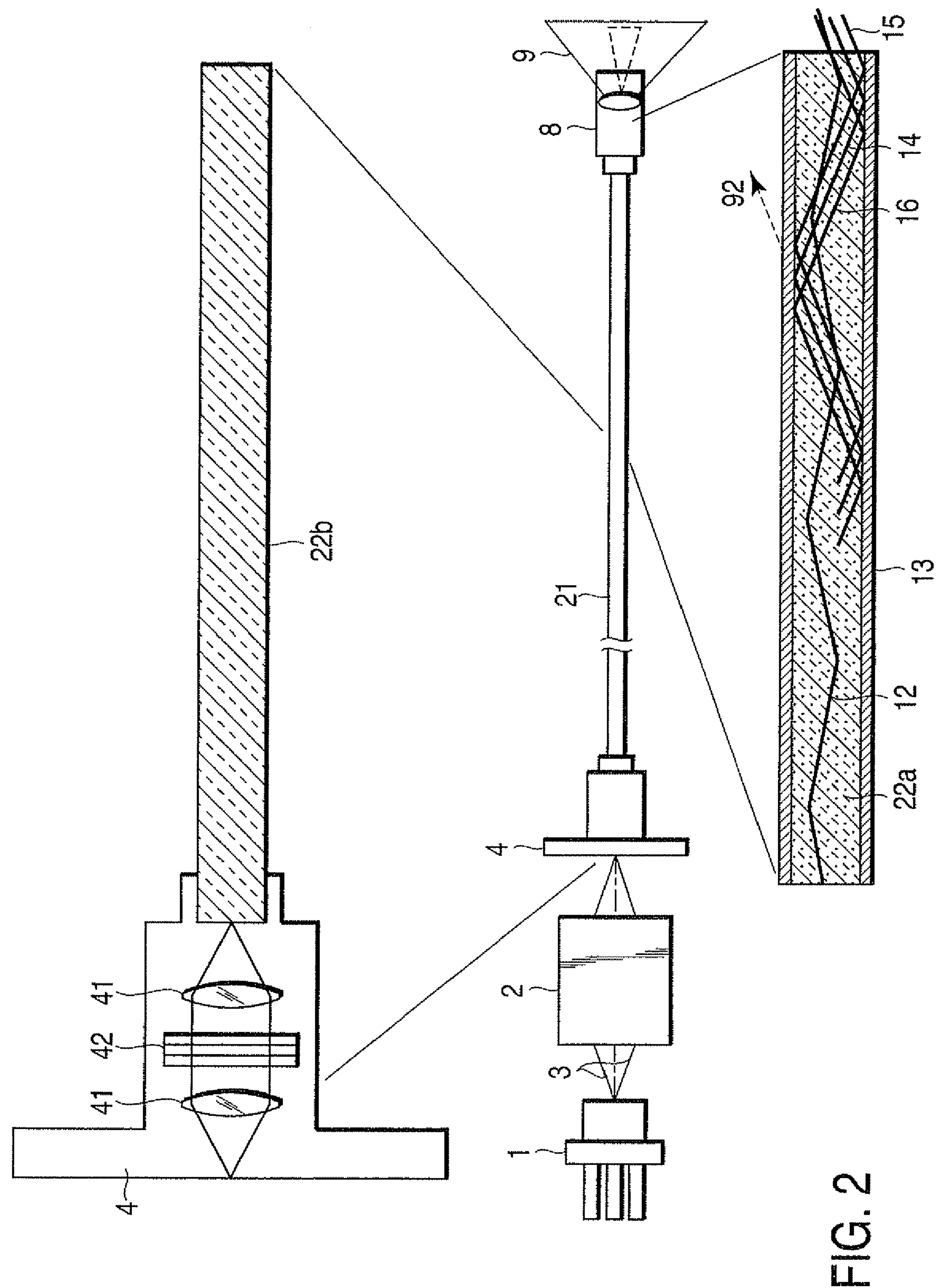
FIG. 2 shows a fiber light source according to the second embodiment.

FIG. 2 shows a fiber light source according to the second embodiment. The same reference numerals as in the first embodiment shown in FIG. 1 denote the same members in FIG. 2, and a detailed description thereof will be omitted. A description of portions common to those of the first embodiment will be omitted, and portions different from the first embodiment will be described below.

A fiber light source of the second embodiment comprises an optical fiber 21 in pace of the first optical fiber 5, the connector 6, and the second optical fiber 7 in the first embodiment. The optical fiber 21 includes a light guide member 22. Part of the light guide member 22 that is located near the exit end in the longitudinal direction contains phosphors while the remaining portion contains no phosphor. That is, the light guide member 22 has a phosphor-containing portion 22*a* and a non-phosphor portion 22*b*. The phosphor-containing portion 22*a* is located near the exit end of the optical fiber 21. The details of phosphors contained in the light guide member 22 are the same as those in the first embodiment. The optical fiber 21 also has a metal film 13 covering the outer surface of a portion in which fluorescence emitted from phosphors travels toward the exit end. That is, the metal film 13 covers the outer surface of a portion of the light guide member 22 that contains phosphors, i.e., the phosphor-containing portion 22*a*. However, the metal film 13 may cover the outer surface of a portion wider than the phosphor-containing portion 22*a*. That is, the metal film 13 may cover the outer surface of part or all of the non-phosphor portion 22*b* in addition to the phosphor-containing portion 22*a*. A dichroic mirror 42 that transmits exciting light and reflects fluorescence is placed between lenses 41 in a fiber connector 4 like the connector 6 in the first embodiment. The dichroic mirror 42 is placed between a semiconductor laser 1 as an exciting light source and the optical fiber 21 containing phosphors.

The second embodiment can obtain the same advantages as those of the first embodiment.

Third Embodiment

Figure 3:
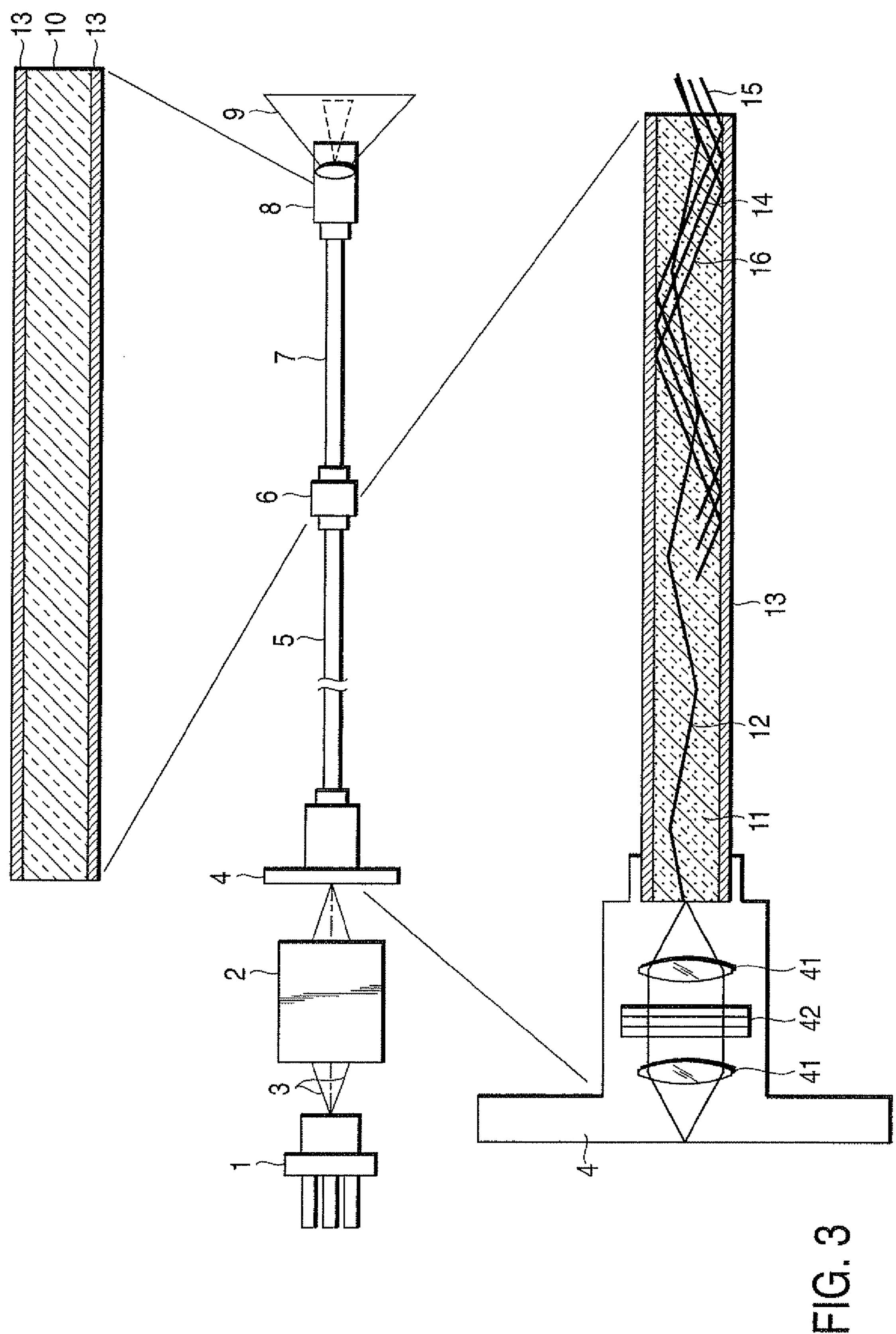
FIG. 3 shows a fiber light source according to the third embodiment.

FIG. 3 shows a fiber light source according to the third embodiment. The same reference numerals as in the first embodiment shown in FIG. 1 denote the same members in FIG. 3, and a detailed description thereof will be omitted. A description of portions common to those of the first embodiment will be omitted, and portions different from the first embodiment will be described below.

According to the third embodiment, a first optical fiber 5 includes a light guide member 11 containing phosphors and a metal film 13 covering the outer surface of the light guide member 11. A second optical fiber 7 includes a light guide member 10 containing no phosphor and a metal film 13 covering the outer surface of the light guide member 10. The first optical fiber 5 and the second optical fiber 7 comprise the same structure except that one of the light guide members contains no phosphor. In a fiber connector 4, a dichroic mirror 42 that transmits exciting light and reflects fluorescence is placed between lenses 41 like the fiber connector 4 in the second embodiment. The dichroic mirror 42 is placed between a semiconductor laser 1 as an exciting light source and the first optical fiber 5 containing phosphors. The details of phosphors contained in the first optical fiber 5 are the same as those in the first embodiment.

According to this embodiment, the first optical fiber 5 on the side where exciting light strikes contains phosphors, and the second optical fiber 7 on the side where light exits contains no phosphor. As fluorescence is emitted, thus, heat is not generated on the light exit end side but is generated on the exciting light incident end side. Accordingly, the heat generated in a portion near the exit end is small. Placing a heat dissipation structure at a portion near the exciting light incident end further facilitates heat dissipation design.

In this embodiment, since the first optical fiber 5 and the second optical fiber 7 comprise the same structure except that one of the fibers contains no phosphor. This provides an advantage of increasing the coupling efficiency between the first optical fiber 5 and the second optical fiber 7.

Fourth Embodiment

Figure 4:
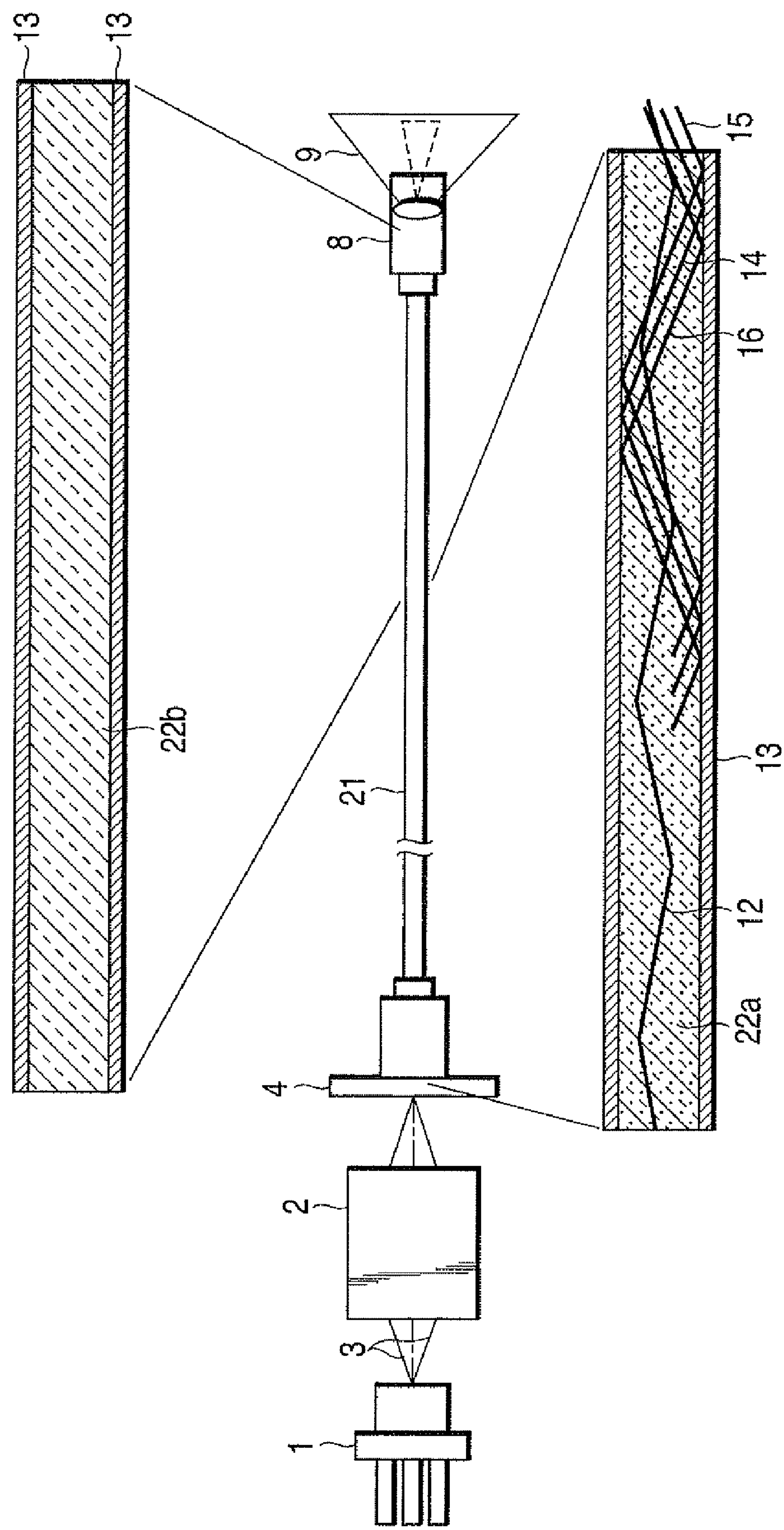
FIG. 4 shows a fiber light source according to the fourth embodiment.

FIG. 4 shows a fiber light source according to the fourth embodiment. The same reference numerals as in the second embodiment shown in FIG. 2 denote the same members in FIG. 4, and a detailed description thereof will be omitted. A description of portions common to those of the second embodiment will be omitted, and portions different from the second embodiment will be described below.

An optical fiber 21 includes a light guide member 22. Part of the light guide member 22 that is located near the incident end in the longitudinal direction contains phosphors while the remaining portion contains no phosphor. That is, the light guide member 22 has a phosphor-containing portion 22*a* and a non-phosphor portion 22*b*. The phosphor-containing portion 22*a* is located near the incident end of the optical fiber 21. The optical fiber 21 also has a metal film 13 covering the outer surface of a portion in which fluorescence emitted from phosphors travels toward the exit end. That is, the metal film 13 covers the entire outer surface of the light guide member 22. Note that the internal arrangement of a fiber connector 4 is the same as that in the second embodiment. In addition, the internal arrangement of a fiber connector 4 in each embodiment described below remains the same.

According to this embodiment, the portion on the exciting light incident side contains phosphors, and the portion on light exit side contains no phosphor. For this reason, as fluorescence is emitted, heat is not generated on the light exit end side but is generated on the exciting light incident end side. Accordingly, the heat generated on a portion near the light exit end is small. Placing a heat dissipation structure at a portion near the exciting light incident end further facilitates heat dissipation design.

Fifth Embodiment

Figure 5:
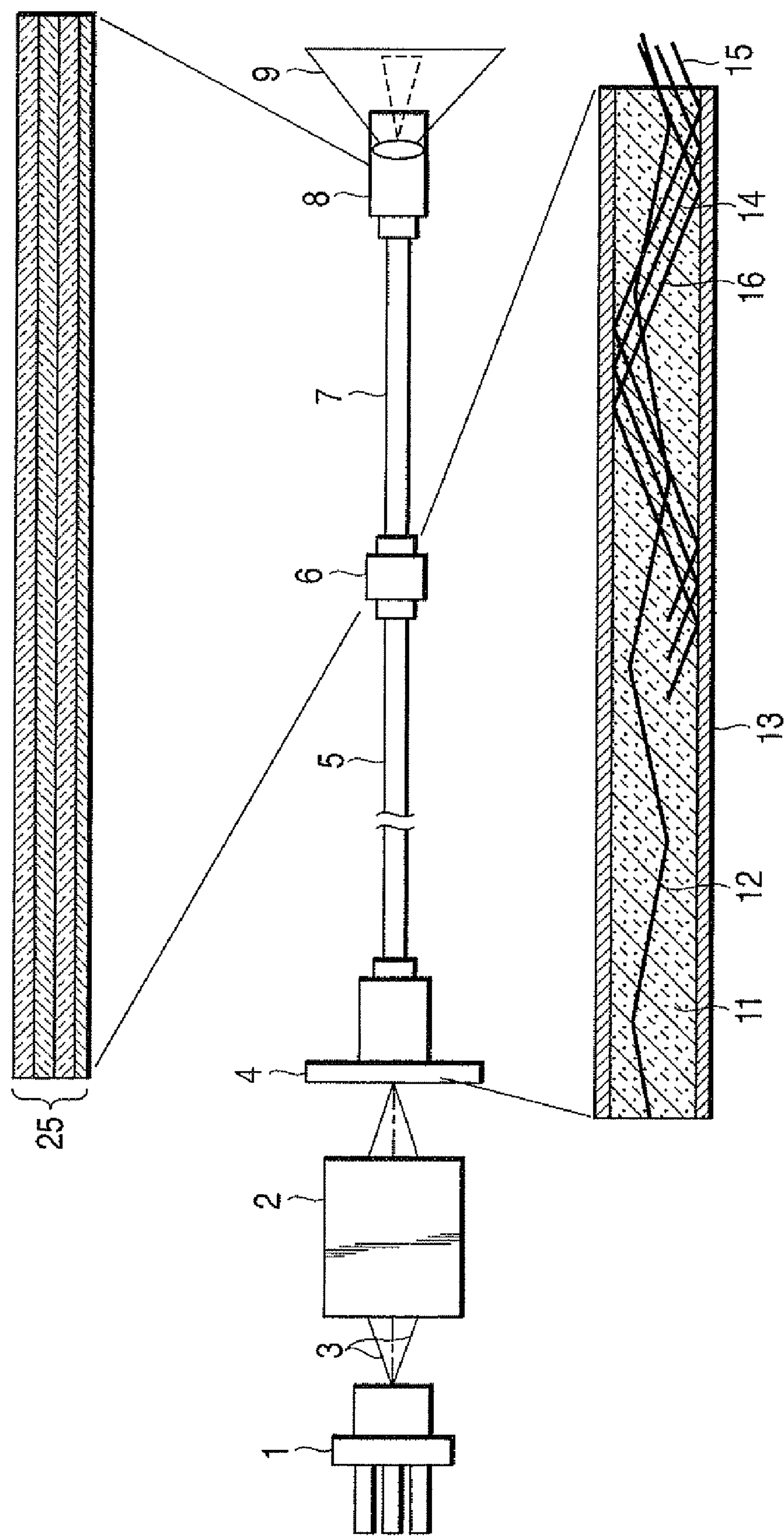
FIG. 5 shows a fiber light source according to the fifth embodiment.

FIG. 5 shows a fiber light source according to the fifth embodiment. The same reference numerals as in the third embodiment shown in FIG. 3 denote the same members in FIG. 5, and a detailed description thereof will be omitted. A description of portions common to those of the third embodiment will be omitted, and portions different from the third embodiment will be described below.

According to the fifth embodiment, a second optical fiber 7 comprises a fiber bundle 25 instead of a single fiber with a metal coating. This embodiment thus has an advantage of preventing light scattering/absorption at the interface between the light guide member 10 and the metal film 13 in the third embodiment. The second optical fiber 7 comprises the fiber bundle 25, and hence each fiber constituting the bundle is thin. If, thus, the length of the fiber increases, the fiber becomes susceptible to breakage. Minimizing the length of the fiber can provide a high-efficiency fiber light source resistant to breakage as a whole.

Sixth Embodiment

Figure 6:
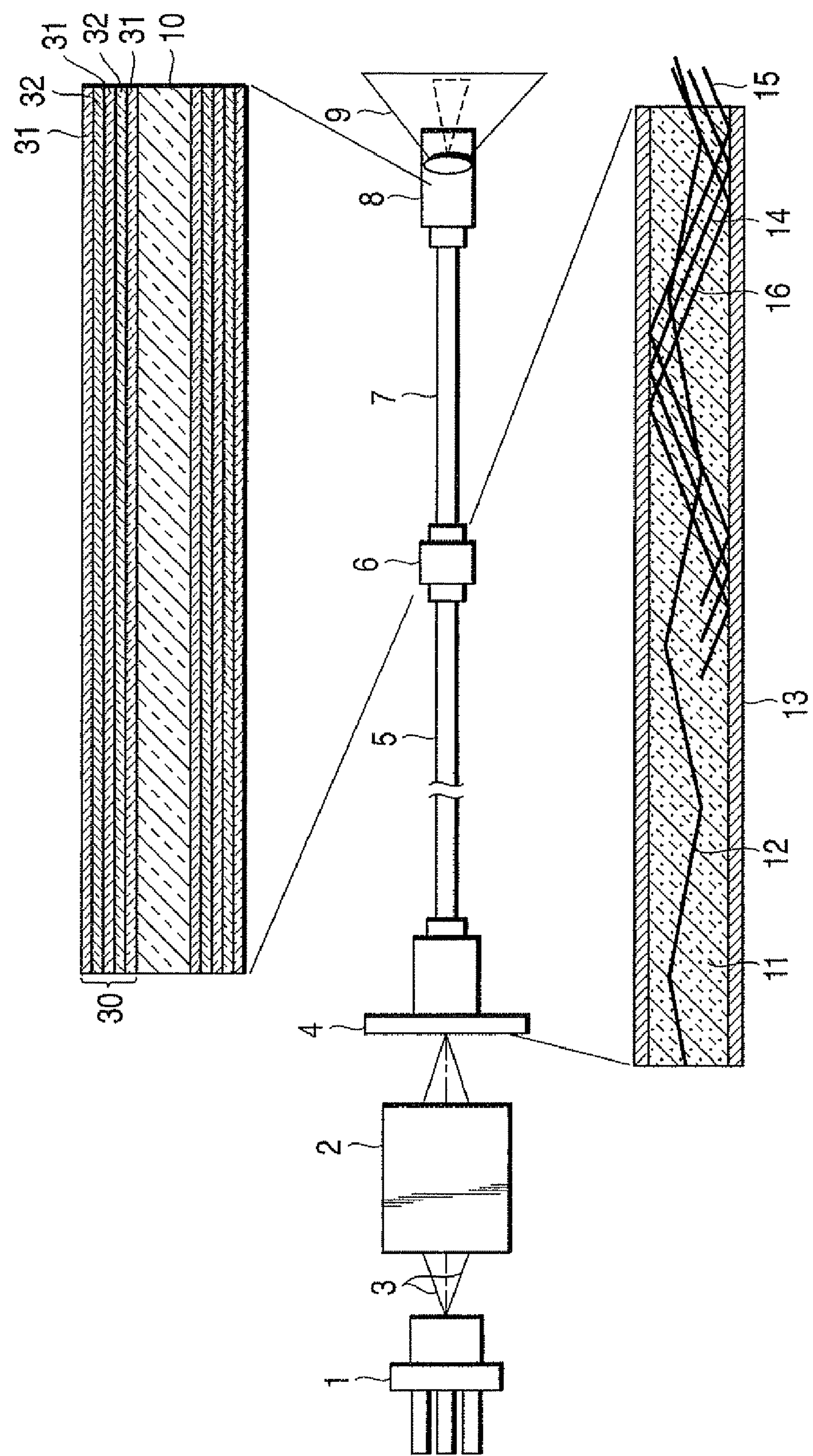
FIG. 6 shows a fiber light source according to the sixth embodiment.

FIG. 6 shows a fiber light source according to the sixth embodiment. The same reference numerals as in the third embodiment shown in FIG. 3 denote the same members in FIG. 6, and a detailed description thereof will be omitted. A description of portions common to those of the third embodiment will be omitted, and portions different from the third embodiment will be described below.

In the sixth embodiment, a second optical fiber 7 has a light guide member 10 containing no phosphor and a dielectric multilayer film 30 covering the outer surface of the light guide member 10. The dielectric multilayer film 30 functions as a high-reflection film. The dielectric multilayer film 30 has a structure in which thin dielectric films 31 and 32 having different reflectance are alternately stacked on the outer surface of the light guide member 10. The thin dielectric films 31 and 32 preferably have a thickness of approximately $\lambda/4$ where $\lambda$ is the peak wavelength of light output from the fiber light source. As a result, owing to multiple reflection, this structure has a higher reflectance than a metal film, and obtains an extra high-efficiency light guiding characteristic because almost no light scattering/absorption occurs at the interface unlike a metal film.

This embodiment can be variously modified. For example, it is possible to design a reflectance-wavelength characteristic by freely designing the structure comprising a multilayer thin dielectric film when guiding light in a very wide wavelength range or guiding only light having a specific wavelength with a small loss.

Seventh Embodiment

Figure 7:
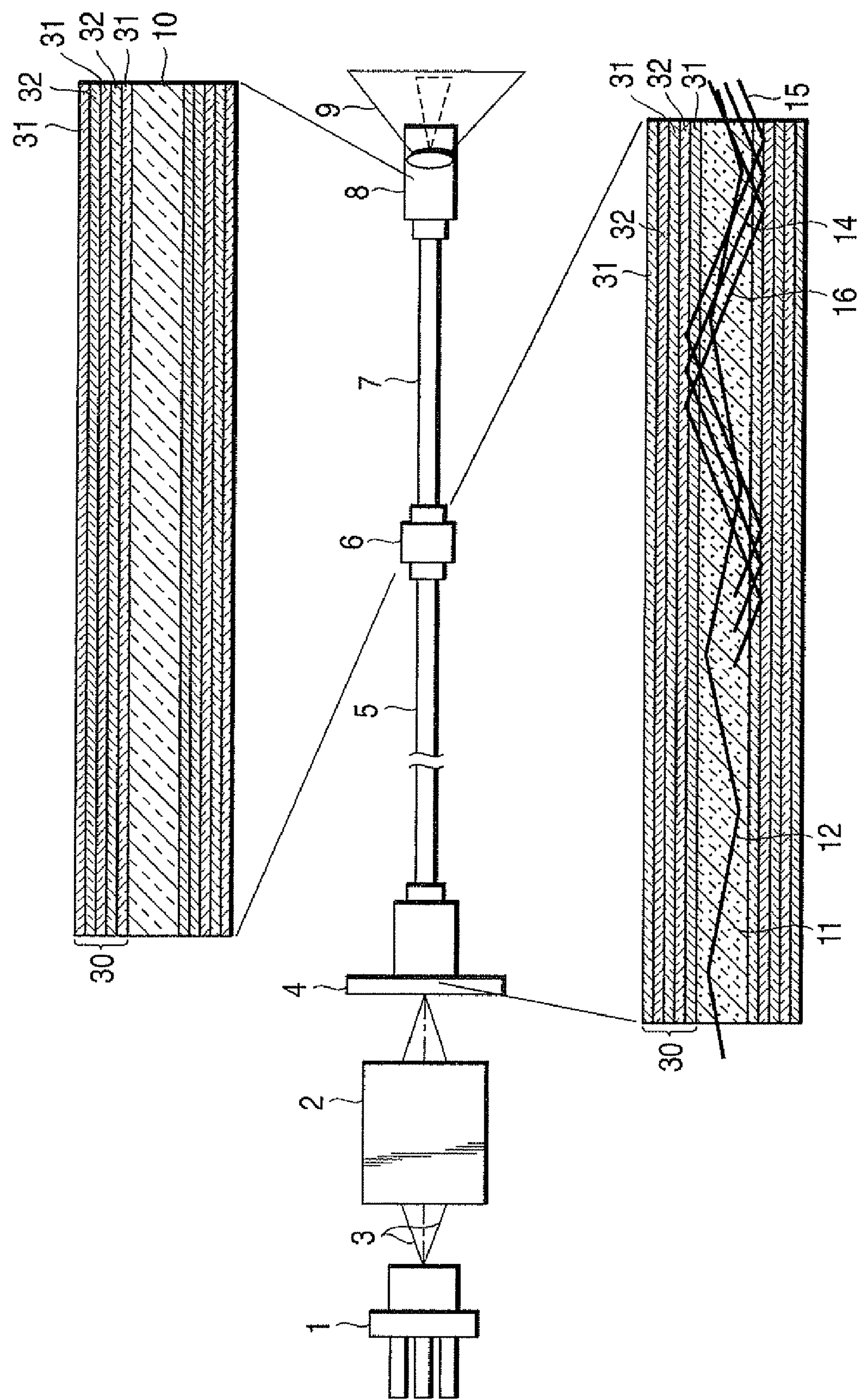
FIG. 7 shows a fiber light source according to the seventh embodiment.

FIG. 7 shows a fiber light source according to the seventh embodiment. The same reference numerals as in the sixth embodiment shown in FIG. 6 denote the same members in FIG. 7, and a detailed description thereof will be omitted. A description of portions common to those of the sixth embodiment will be omitted, and portions different from the sixth embodiment will be described below.

In the seventh embodiment, a first optical fiber 5 has a light guide member 11 containing phosphors and a dielectric multilayer film 30 covering the outer surface of the light guide member 11. The dielectric multilayer film 30 functions as a high-reflection film. The dielectric multilayer film 30 has a structure in which thin dielectric films 31 and 32 having different reflectance are alternately stacked on the outer surface of the light guide member 11. The thin dielectric films 31 and 32 preferably have a thickness of approximately $\lambda/4$ where $\lambda$ is the peak wavelength of light output from the fiber light source. As a result, owing to multiple reflection, this structure has a higher reflectance than a metal film, and obtains an extra high-efficiency light guiding characteristic because almost no light scattering/absorption occurs at the interface unlike a metal film.

In this embodiment, the first optical fiber 5 and a second optical fiber 7 comprise the same structure except that one of the fibers contains no phosphor. This provides an advantage of increasing the coupling efficiency between the first optical fiber 5 and the second optical fiber 7.

Eighth Embodiment

Figure 8A:
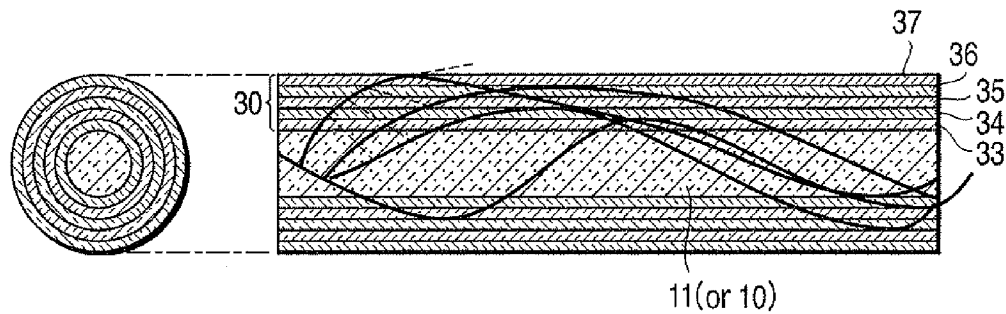
FIG. 8A shows a cross section of an optical fiber and the trajectories of light beams according to the eighth embodiment.
Figure 8B:
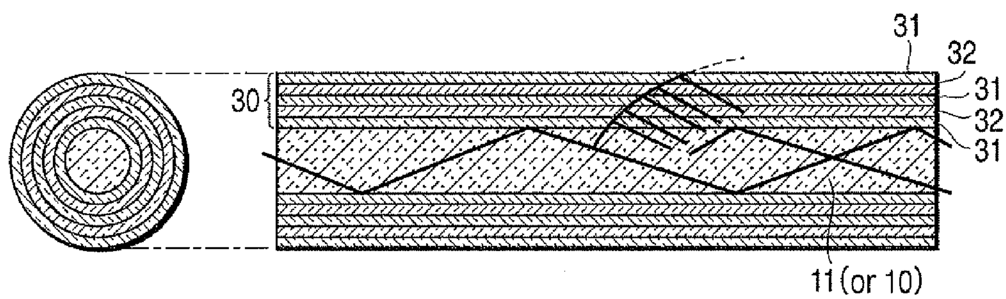
FIG. 8B shows a cross section of the second optical fiber and the trajectories of light beams according to the sixth embodiment.
Figure 8C:
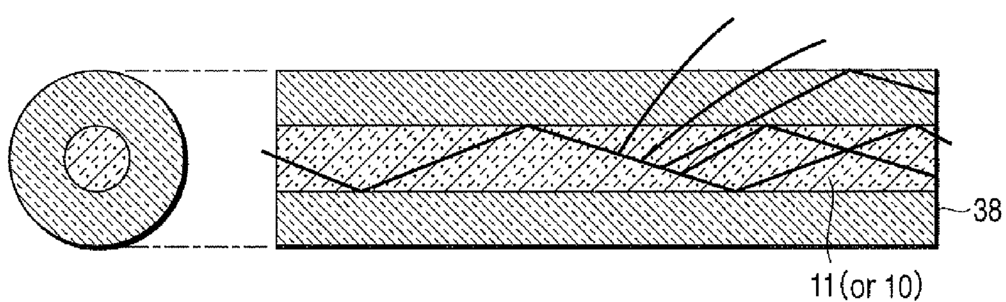
FIG. 8C shows a cross section of a general single fiber and the trajectories of light beams.

This embodiment is directed to another optical fiber in place of the second optical fiber 7 in the sixth embodiment and the first and second optical fibers 5 and 7 in the seventh embodiment. FIG. 8A shows the optical fiber according to this embodiment. In the embodiment, a dielectric multilayer film 30 has a structure in which thin dielectric films 33, 34, 35, 36, and 37 are stacked on a light guide member 11 (or 10) so that their refractive index gradually decreases from the center of the light guide member 11 (or 10) to the outer surface. Using this dielectric film structure can reduce the amount of light that is transmitted through the fiber surface and scattered and obtain a high light guiding efficiency because the incident angles of both exciting light and fluorescence with respect to the outer surface gradually decrease toward the outer surface. For comparison, FIG. 8B shows a cross section of a second optical fiber 7 and the trajectories of light beams according to the sixth embodiment. FIG. 8C shows a cross section of a general single fiber and the trajectories of light beams. The single fiber in FIG. 8C comprises a single-layer dielectric film 38. According to the single fiber in FIG. 8C, a light beam is reflected by only the surface of the dielectric film 38. According to the optical fiber in FIG. 8B, a light beam is reflected by the interfaces between thin dielectric films 31 and 32, but the incident angle of light is constant. Accordingly, the optical fiber in FIG. 8B has a higher light guiding efficiency than the single fiber in FIG. 8C. The optical fiber in FIG. 8A has a higher light guide efficiency than the optical fiber in FIG. 8B.

Ninth Embodiment

This embodiment is directed to a method of manufacturing an optical fiber having a dielectric multiplayer film described in the sixth or seventh embodiment.

Figure 9A:
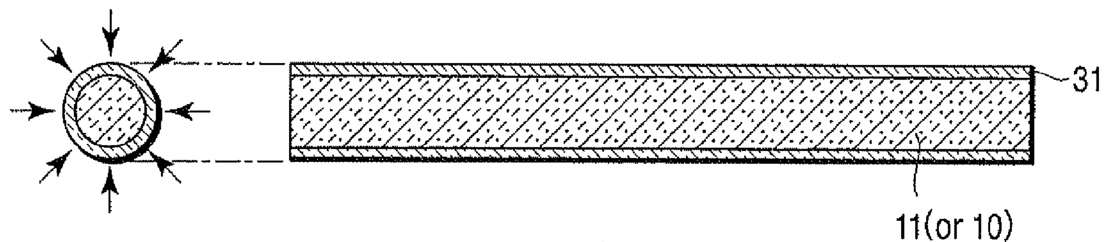
FIG. 9A shows the first step in manufacturing an optical fiber according to the ninth embodiment.

As shown in FIG. 9A, a component material containing a dielectric that forms a thin dielectric film 31 is sprayed against a light guide member 11 (or 10) from outside in the radial direction, or the light guide member 11 (or 10) is dipped in a liquid containing a dielectric that forms the thin dielectric film 31, and the dielectric is cured by heat or ultraviolet light.

Figure 9B:
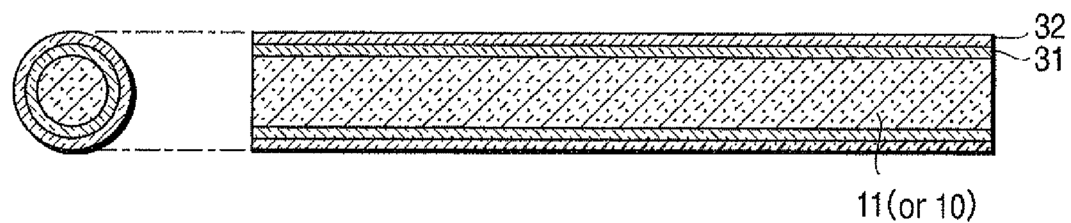
FIG. 9B shows the step following the step in FIG. 9A in manufacturing the optical fiber according to the ninth embodiment.

Subsequently, as shown in FIG. 9B, a component material containing a dielectric that forms a thin dielectric film 32 is sprayed against the structure manufactured in the FIG. 9A from outside in the radial direction, or the structure manufactured in FIG. 9A is dipped in a liquid containing a dielectric that forms the thin dielectric film 32, and the dielectric is cured by heat or ultraviolet light.

Figure 9C:
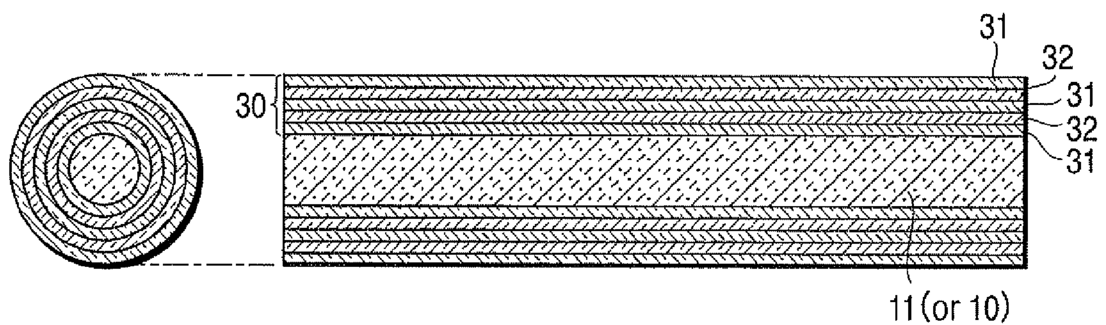
FIG. 9C shows the step following the step in FIG. 9B in manufacturing the optical fiber according to the ninth embodiment.

An optical fiber covered with a dielectric multilayer film 30 is manufactured by repeatedly forming the thin dielectric films 31 and 32, as shown in FIG. 9C.

This technique facilitates manufacturing a dielectric multilayer film and controlling the refractive index and thickness of the dielectric multilayer film.

Although the method of manufacturing the optical fiber according to the sixth or seventh embodiment has been described above, the optical fiber according to the eighth embodiment can be manufactured by the same technique by replacing the thin dielectric films 31 and 32 with the thin dielectric films 33, 34, 35, and 36 that are stacked on the outer surface of the light guide member 11 (or 10).

10th Embodiment

This embodiment is directed to a method of manufacturing an optical fiber having a dielectric multiplayer film described in the sixth or seventh embodiment.

Figure 10A:
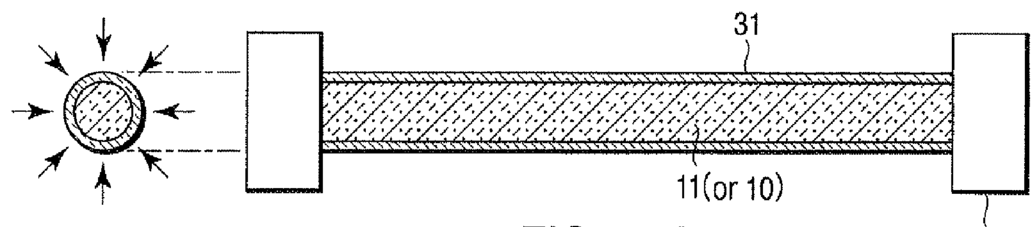
FIG. 10A shows the first step in manufacturing an optical fiber according to the 10th embodiment.

As shown in FIG. 10A, a component material containing a dielectric that forms a thin dielectric film 31 is sprayed against a light guide member 11 (or 10) from outside in the radial direction, or the light guide member 11 (or 10) is dipped in a liquid containing a dielectric that forms only the thin dielectric film 31, and the dielectric is cured by heat or ultraviolet light. In this case, an end portion of the light guide member 11 (or 10) is fixed by a fixing member 40. The fixing member 40 is preferably a porous member or a mesh member.

Figure 10B:
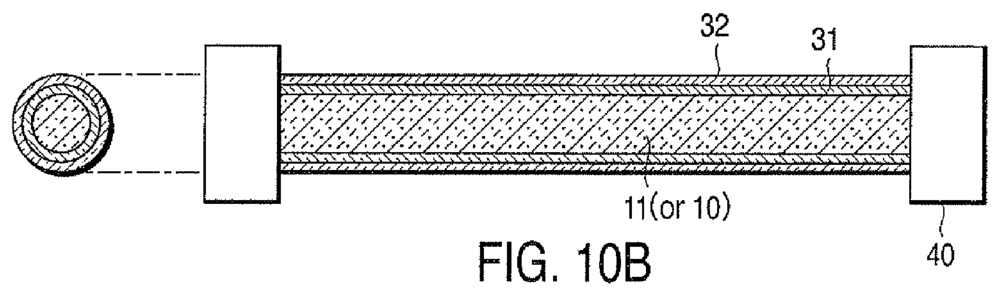
FIG. 10B shows the step following the step in FIG. 10A in manufacturing the optical fiber according to the 10th embodiment.

Subsequently, as shown in FIG. 10B, a component material containing a dielectric that forms a thin dielectric film 32 is sprayed against the structure manufactured in the FIG. 10A from outside in the radial direction, or the structure manufactured in FIG. 10A is dipped in a liquid containing a dielectric that forms the thin dielectric film 32, and the dielectric is cured by heat or ultraviolet light.

Figure 10C:
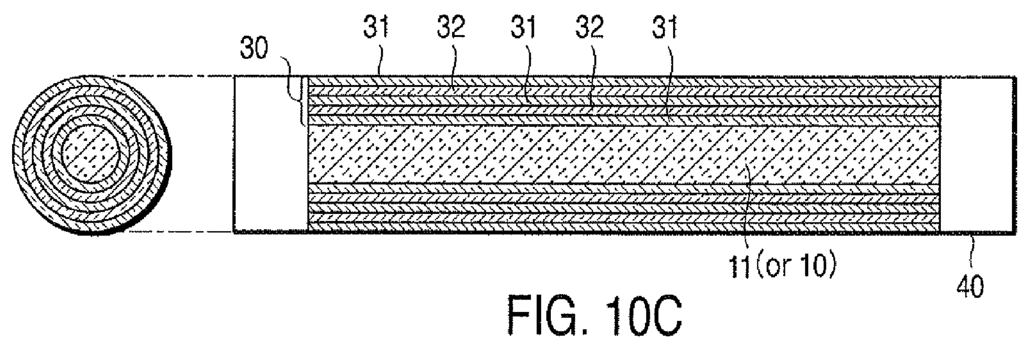
FIG. 10C shows the step following the step in FIG. 10B in manufacturing the optical fiber according to the 10th embodiment.
Figure 10D:
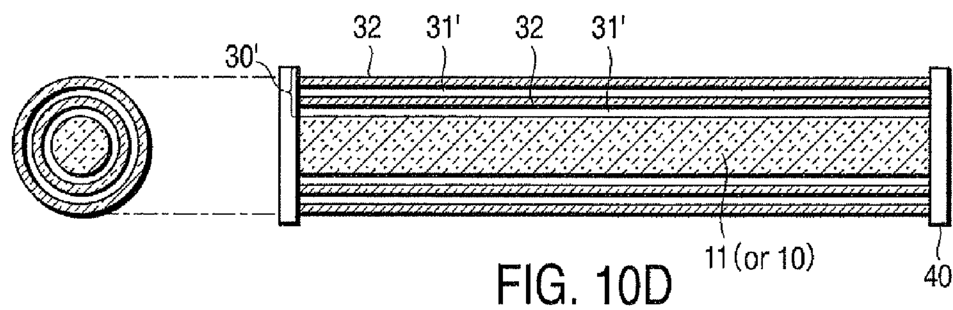
FIG. 10D shows the step following the step in FIG. 10C in manufacturing the optical fiber according to the 10th embodiment.

An optical fiber comprising a dielectric multilayer film 30 on the outer surface is manufactured by repeatedly forming the thin dielectric films 31 and 32, as shown in FIG. 10C.

The structure manufacturing in FIG. 10C is dipped in a liquid that etches the thin dielectric film 31 having a low refractive index. This forms an air layer 31' in the place where the thin dielectric film having a low refractive index has existed, resulting in a further reduction in refractive index. This further increases the reflectance of a dielectric multilayer film 30'.

If the fixing member 40 is a transparent member, the member is cut thin, and the resultant structure may be used as an optical fiber without any change. Alternatively, the respective thin dielectric films may be fixed through porous portions by using an adhesive.

This technique facilitates manufacturing a dielectric multilayer film and can implement light guiding with higher efficiency by removing a layer of the dielectric multilayer film that has a low refractive index and increasing the reflectance.

This embodiment can be variously modified. In order to form the air layer 31', the embodiment uses the technique of etching a thin dielectric film by using a liquid. However, the embodiment may use another technique that can remove a dielectric material, e.g., a technique such as dry etching or heating/sublimation.

Although the embodiments of the present invention have been described with reference to the views of the accompanying drawing, the present invention is not limited to these embodiments. The embodiments can be variously modified and changed within the spirit and scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A fiber light source comprising:

an exciting light source to emit exciting light; and an optical fiber to guide the exciting light, wherein:

the optical fiber comprising a first optical fiber and a second optical fiber separated from each other, the second optical fiber containing phosphors that emit fluorescence in accordance with the application of exciting light, and including a high reflection film covering an outer surface thereof, the content of the phosphors and the type of the phosphors being controlled to provide a desired optical output characteristic;

the first and second optical fibers are detachably attached through a connector such that the second optical fiber can be changed to vary at least one of a content and type of phosphors therein; and the phosphors include different types of phosphors that are excited by the exciting light to emit fluorescence components with different optical spectra, and the different types of phosphors are respectively contained in different regions of the second optical fiber in the longitudinal direction.

2. The fiber light source according to claim 1, wherein the high reflection film comprises a metal film.

3. The fiber light source according to claim 1, wherein the high reflection film comprises a laminated film including a metal film and a dielectric film.

4. The fiber light source according to claim 1, wherein the high reflection film comprises a dielectric multilayer film.

5. The fiber light source according to claim 4, wherein the dielectric multilayer film has a structure in which thin dielectric films having different refractive index are alternately stacked.

6. The fiber light source according to claim 5, wherein the thin dielectric films have a thickness of approximately $\lambda/4$ where $\lambda$ is the peak wavelength of light output from the fiber light source.

7. The fiber light source according to claim 4, wherein the dielectric multilayer film has a structure in which the thin dielectric films are stacked on the optical fiber so that the refractive index of the thin dielectric films gradually decreases from the center of the optical fiber to the outer surface.

8. The fiber light source according to claim 1, wherein the phosphors emit fluorescence of a color complementary to that of exciting light.

9. The fiber light source according to claim 1, wherein the phosphors emit fluorescence of multiple colors.

10. The fiber light source according to claim 1, further comprising an optical functional component to transmit exciting light and to reflect fluorescence between the exciting light source and the second optical fiber.

* * * * *